US010274462B2

(12) United States Patent
Restivo et al.

(10) Patent No.: US 10,274,462 B2
(45) Date of Patent: Apr. 30, 2019

(54) DEVICE FOR MEASURING MATERIAL DETERIORATION IN EQUIPMENT

(71) Applicant: Savannah River Nuclear Solutions, LLC, Aiken, SC (US)

(72) Inventors: Michael L. Restivo, Aiken, SC (US); Kenneth J. Imrich, Grovetown, GA (US); Samuel D. Fink, Aiken, SC (US); Mark R. Duignan, Evans, GA (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 156 days.

(21) Appl. No.: 15/492,783

(22) Filed: Apr. 20, 2017

(65) Prior Publication Data

US 2018/0306699 A1 Oct. 25, 2018

(51) Int. Cl.
*G01N 17/04* (2006.01)
*G01N 29/04* (2006.01)

(52) U.S. Cl.
CPC ............ *G01N 29/04* (2013.01); *G01N 17/043* (2013.01); *G01N 17/046* (2013.01)

(58) Field of Classification Search
CPC ...... G01N 29/04; G01N 29/07; G01N 29/223; G01N 29/2475; G01N 29/4427; G01N 17/00; G01N 17/006; G01N 17/04; G01N 17/043; G01N 17/046
See application file for complete search history.

(56) References Cited

U.S. PATENT DOCUMENTS

| | | | | |
|---|---|---|---|---|
| 3,236,096 A | * | 2/1966 | Macatician | G01N 3/56 324/700 |
| 4,097,341 A | * | 6/1978 | Schell | G01N 17/00 165/11.1 |
| 4,393,711 A | | 7/1983 | Lapides | |
| 4,510,793 A | * | 4/1985 | Ploegaert | G01B 17/02 73/597 |
| 4,539,846 A | * | 9/1985 | Grossman | G01N 17/00 422/53 |
| 4,872,345 A | * | 10/1989 | Dicks | G01B 17/02 73/597 |
| 4,935,884 A | | 6/1990 | Hajicek | |
| 6,131,659 A | * | 10/2000 | Johnson | E21B 47/00 166/242.4 |
| 6,357,470 B1 | * | 3/2002 | Evans | F16L 41/16 137/315.01 |
| 6,578,422 B2 | * | 6/2003 | Lam | G01N 29/0609 73/620 |

(Continued)

FOREIGN PATENT DOCUMENTS

CN 104122192 10/2014

*Primary Examiner* — Helen C Kwok
(74) *Attorney, Agent, or Firm* — Dority & Manning, P.A.

(57) ABSTRACT

A device for improving the accuracy and precision of measuring equipment changes due to corrosion, erosion, build-up of material, and combinations thereof. Increased control over the placement and removal of a coupon within the equipment is provided. Embodiments of the coupon provide multiple approaches for such measurements such as e.g., weight changes, thickness changes, inspection and analysis of the contacting surface of the coupon, and combination. Improved measurements with coupons using probes such as e.g., ultrasonic transducers is also described.

20 Claims, 10 Drawing Sheets

(56) References Cited

U.S. PATENT DOCUMENTS

| | | |
|---|---|---|
| 7,541,817 B2 | 6/2009 | Nielsen et al. |
| 7,779,694 B2 | 8/2010 | Iizuka |
| 8,266,964 B2 | 9/2012 | Iizuka et al. |
| 8,806,944 B2 | 8/2014 | Grubb et al. |
| 2002/0078752 A1* | 6/2002 | Braunling .............. G01N 17/04 73/627 |
| 2007/0159187 A1 | 7/2007 | Chen et al. |
| 2013/0191038 A1 | 7/2013 | Wolf et al. |
| 2016/0109413 A1* | 4/2016 | Bonadies, Jr. ......... G01N 29/07 73/598 |

* cited by examiner

DEVICE FOR MEASURING MATERIAL DETERIORATION IN EQUIPMENT

FEDERAL RESEARCH STATEMENT

This invention was made with Government support under Contract No. DE-AC09-085R22470, awarded by the U.S. Department of Energy. The Government has certain rights in the invention.

FIELD OF THE INVENTION

The subject matter of the present disclosure relates generally to a device for measuring changes that can occur in various processing equipment due to corrosion, erosion, build-up of material, and combinations of the same.

BACKGROUND OF THE INVENTION

Systems that transport and process liquids, or slurries containing liquids and solids, or gas streams containing solids are ubiquitous in chemical processing, raw material mining, manufacturing and storage operations. Such process streams may contain one or more components that cause erosion, corrosion, and other changes in the equipment making up such systems. For example, slurries contain particles that may be very abrasive thereby causing erosion as the particles travel through piping, move through tanks, or are otherwise manipulated in the equipment. Various liquids may contain components that react with the metals to cause corrosion of the equipment. Some liquids may cause material loss or damage to the equipment by both corrosion and erosion. In other liquids, scale may undesirably build up in the equipment.

Certain techniques may be employed to identify material loss or other damage. A portion of equipment such as a section of piping could be removed and the interior can be visually inspected or the thickness of the pipe wall could be measured and compared to a previously measured thickness. However, this technique likely requires stopping the use of the equipment, e.g., flow through the piping, which is disruptive of the manufacturing process. Removal of a portion of the equipment such as the piping and/or the measurement technique may require unacceptable, destructive methods.

In another conventional approach, a coupon constructed of a known material is placed into contact with the liquid being transported or processed. In this conventional construction, the coupon may be in the form of a circular section of pipe. After an interval of time, the coupon is removed for inspection to determine whether material loss or damage has occurred. This approach also has disadvantages. For example, installation and removal of the coupon may still require interruption of the manufacturing process depending upon the configuration of the coupon. Installation and removal of the coupon may also affect the accuracy of the testing. The coupon may be damaged by unintended removal of material such as removal of a portion of the coupon or removal of scale, oxides, or other coatings that may have formed. Removing the coupon and exposing it to e.g., air or humid air could also affect accuracy as chemical reactions may occur as a result. Changes in temperature between the coupon in-situ and the coupon removed could also affect the result.

In addition, the accuracy of such coupon testing can be significantly impacted by how the coupon is placed into the liquid flow path. For example, placing the coupon directly into the path of flow may lead to an incorrect, exaggerated measurement. The rate of removal of material from a coupon by e.g., particles from a slurry is known to be highly dependent on the geometry and location of the coupon. Furthermore, the presence of the coupon may interrupt the normal path of fluid and thereby result in measuring inaccurate wear rates.

Accordingly, a device for detecting corrosion or erosion occurring in various equipment including e.g., piping systems would be useful. Such a device that can be used to determine e.g., whether scale or other deposits are building up on the equipment, whether material losses from corrosion or erosion are occurring, estimating the amount of build-up or material losses, and combinations thereof would be particularly helpful.

BRIEF DESCRIPTION OF THE INVENTION

The present invention provides a device for improving the accuracy and precision of measuring changes that can occur in equipment due to corrosion, erosion, build-up of material, and combinations thereof. The device allows for increased control over the placement and removal of a coupon within the equipment. Impact on the fluid dynamics of the process can be minimized. The coupon provides multiple approaches for such measurements such as e.g., weight changes, thickness changes, inspection and analysis of the contacting surface of the coupon, and combinations thereof. In certain embodiments, the device can provide for improved measurements of coupons using probes such as e.g., ultrasonic transducers. The concurrent enhancements in accuracy, precision, and in a reliably repeating coupon placement location can also yield faster measurements of high fidelity data resulting in lower risk of catastrophic loss of equipment integrity as well as reduced expenditures in processing or testing time to obtain the needed information. Additional aspects and advantages of the invention will be set forth in part in the following description, or may be apparent from the description, or may be learned through practice of the invention.

In one exemplary embodiment, the present invention provides a device for measuring material deterioration in equipment. The device includes a coupon configured for selective insertion and removal through an opening in the equipment. The coupon can include a fluid contacting surface for positioning within an interior of the equipment and in contact with a fluid, a chamber internal to the coupon and having an opening for access thereto, the chamber defined at least in part by a probe facing surface positioned opposite to the fluid contacting surface. A fastener provides for selectively affixing the coupon to the equipment. The fastener is positioned outside of the equipment.

In another exemplary embodiment, the present invention provides a device for measuring material deterioration in equipment. The device includes a coupon configured for insertion and removal through an opening in the equipment. The opening has a surrounding interior surface formed from an equipment material. The coupon can include a fluid contacting surface for positioning within an interior of the equipment and in contact with a fluid, wherein the fluid contacting surface is flush with the surrounding interior surface of the equipment and consisting of the equipment material. A fastener is configured for selectively affixing the coupon to the equipment. The fastener is positioned outside of the equipment. A gap is formed between the fluid contacting surface and the surrounding interior surface and may have a size in the range of 0.0025 inches to 0.0050 inches.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

The use of the same or similar reference numerals in the figures denotes the same or similar features unless otherwise indicated.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 1:
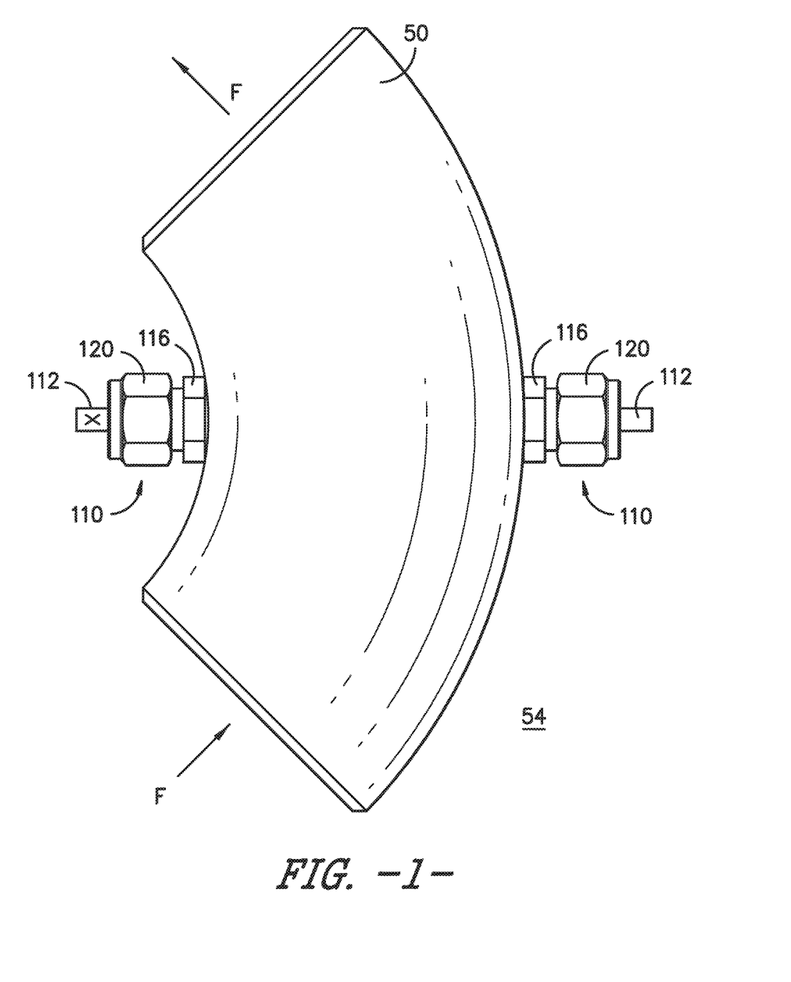
FIG. 1 provides a side view of exemplary embodiments of the invention installed in an example of equipment.
Figure 2:
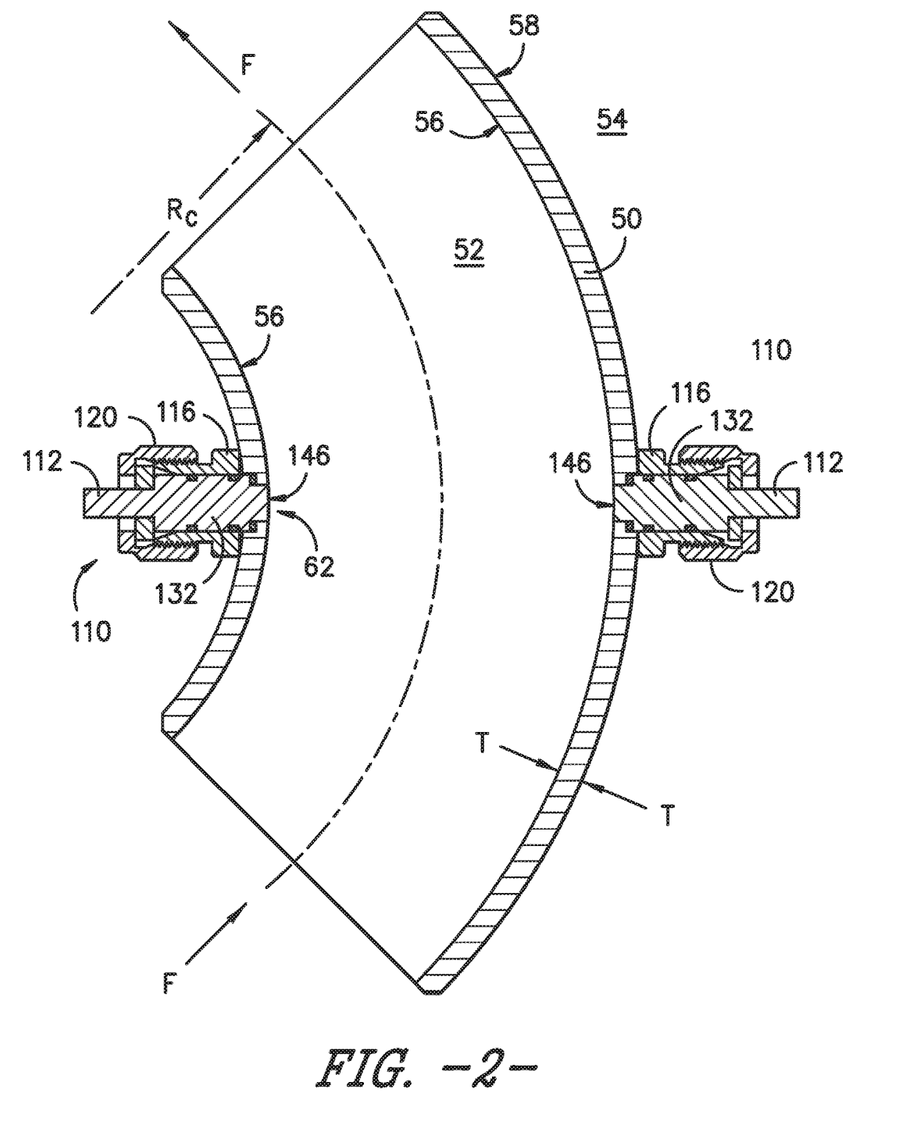
FIG. 2 is a cross-sectional view of the embodiments and equipment of FIG. 1.
Figure 3:
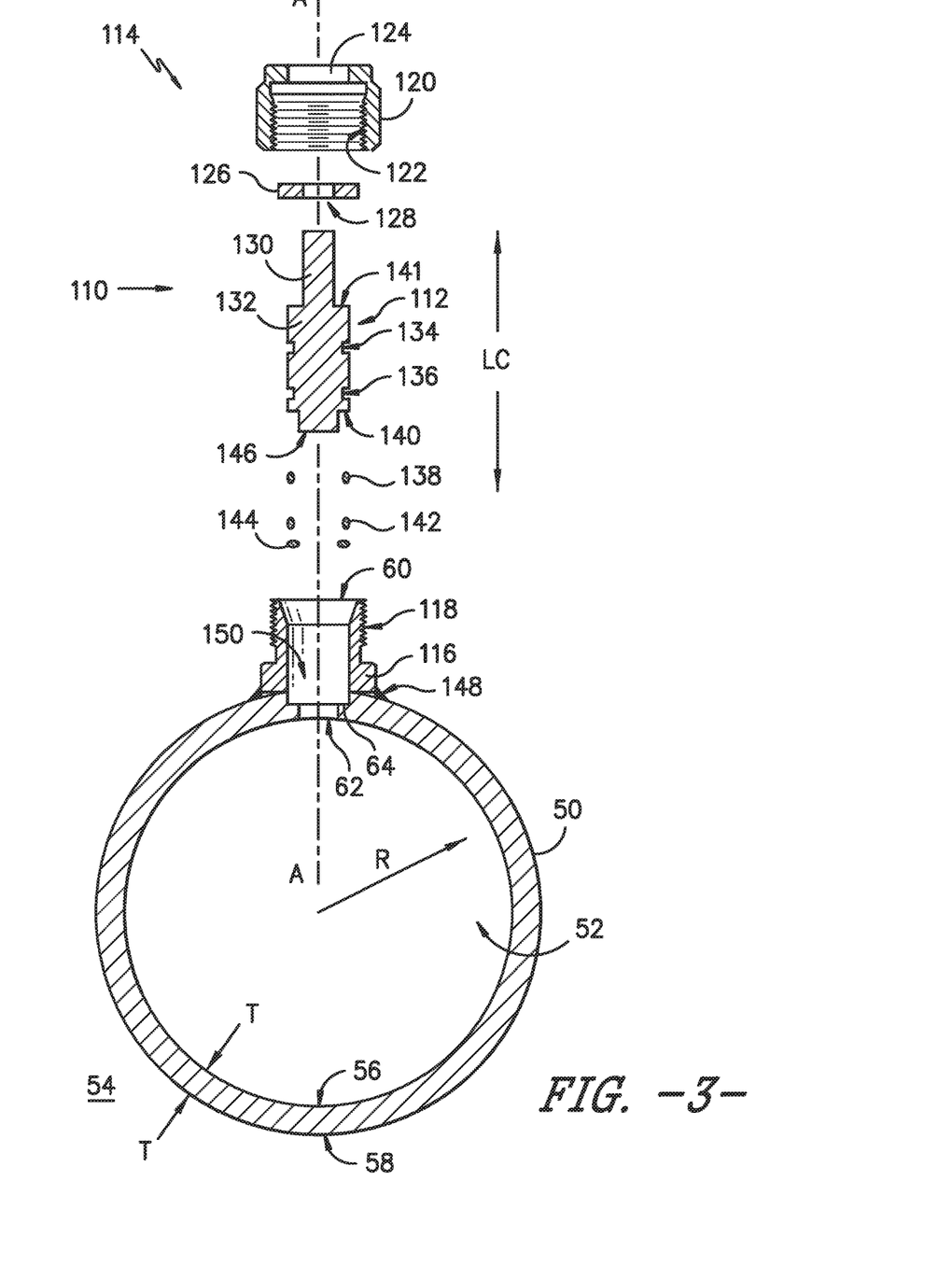
FIG. 3 is a cross-sectional and exploded view of one of the exemplary embodiments of FIGS. 1 and 2 installed in an example of equipment.

FIGS. 1, 2, and 3 provide views of an exemplary embodiment of a device 110 for measuring material deterioration in equipment, which in this example is a pipe 50. As used herein, "material deterioration" refers generally to changes on, or at, a surface of equipment due to any one of, or combinations of, processes such as corrosion (including oxidation), erosion, scaling, and other processes that adversely affect the material from which the equipment is constructed. Thus, "material deterioration" can include processes that may remove material from interior surface 52 by erosion, corrosion, or both; and includes processes that may add material to interior surface 52 by e.g., scaling or other deposit formation.

While a pipe 50 is used by way of example, one of ordinary skill in the art will understand from the teachings herein that the present invention is not limited to use with piping. Instead, the present invention could be employed with various equipment including e.g., tanks, columns, storage vessels, reactors, and others. The equipment may be constructed from a variety of materials including e.g., metals, plastics, or combinations. An exemplary device of the present invention may be used to e.g., measure material deterioration at a surface or wall where equipment is in contact with one or more materials of a process such as dry particulates, slurries, gases, liquids, mixtures, and combinations. The process may be relatively stagnant such as powder or liquid within a tank or may be moving such a flow through a pipe. Using pipe 50 for example, the present invention could be used where the process includes e.g., gas expected to cause corrosion of pipe 50, gas laden with particulates that cause erosion of pipe 50, liquid moving through pipe 50, and others as well.

As shown, for this exemplary embodiment, device 110 includes a coupon 112 that is inserted into an opening 62 in pipe 50. While coupon 112 may be constructed from variety of different materials, for this embodiment coupon 112 is constructed from the same material (sometimes referred to herein as the equipment material) as pipe 50. For example, coupon 112 could be constructed from an alloy having the same composition as the alloy used for pipe 50 or at least interior surface 56. Ideally, coupon 112 may even be constructed from the same lot of equipment material as used to make pipe 50. For example, if pipe 50 is constructed from a particular steel and nickel alloy, coupon 112 could be constructed from the same alloy in order to provide a more accurate measurement of material deterioration in pipe 50. Because the alloy could still have slight differences in composition and crystalline structure, accuracy can be further improved by constructing coupon 112 from the same lot of material used to make pipe 50—though such may not always be possible or practical. In an alternative embodiment, only a portion of coupon 112 near surface 146 is constructed from a material that is the same, or similar to, the material use for pipe 50. In another embodiment, surface 146 of coupon 112 is finished in the same manner that is used for the interior contact surface 56.

Coupon 112 includes a fluid contacting surface 146 that is positioned within the interior 52 of pipe 50 through opening 62 so as to experience the same processes of material deterioration as interior surface 56. Thus, fluid contacting surface 146 and the interior surface 56 of pipe 50 are exposed to the same fluids for the same time intervals. For example, a variety of different gases, liquids, and combinations thereof may be present in pipe 50 including e.g., slurries, highly reactive liquids, radioactive materials, and others that may be detrimental to the expected lifetime of pipe 50.

In addition, for this exemplary embodiment, coupon 112 does not protrude into the flow F of liquid. Such is controlled by e.g., the overall length of coupon 112 and the construction of fastener 114 (FIG. 3), which includes base 116 and nut 120. In one exemplary aspect of the present invention, fluid contacting surface 146 is flush with interior surface 56 surrounding fluid contacting surface 146 as shown in FIG. 2. As used herein, "flush" means that the difference in level between fluid contacting surface 146 and interior surface 56 is 0.02 of an inch or less. For example, in one exemplary aspect, the difference in level between fluid contacting surface 146 and interior surface 56 is 0.008 of an inch or less. By controlling the amount of protrusion (whether above or below surface 56), coupon 112 and particularly fluid contacting surface 146 are not exposed to different fluid transport dynamics and effects than interior surface 56—thereby increasing the accuracy of using device 110 in determining the material deterioration of pipe 50. Stated alternatively, as shown in FIG. 2, pipe 50 has a wall thickness T that may be adversely affected by the flow of fluid F. Device 110 allows for careful control of the amount of protrusion of coupon 112 into the flow F so that the same material deterioration occurs between surfaces 56 and 146. One advantage of such feature is an increase in the accuracy of e.g., measuring changes in thickness T and or changes occurring along surface 146 for purposes of investigating the changes occurring along equipment surface 56. As already set forth, in certain embodiments, accuracy is further improved by matching the materials used for fabricating coupon 112 with those used for pipe 50.

In still other embodiments, fluid contacting surface 146 may have a contour or shape that matches the shape of the interior surface of the equipment. In FIG. 2, for example, pipe 50 and interior surface 56 are shown to have the same radius of curvature $R_C$. Fluid contacting surface 146 may be provided with the same radius of curvature $R_C$ to minimize its exposure to fluid transport dynamics and effects different from that of interior surface 56. A mark or other indicia X (FIG. 1) may also be placed on coupon 112 to ensure that it is properly oriented relative to pipe 50. In addition, such indicia X can also allow an operator to remove and reinstall coupon 112 with the same orientation so that exposure to fluid flow F is consistent between measurements. Indicia X could be also be used to ensure the grain orientation of material in coupon 112 matches interior surface 56 of pipe 50 in cases where such are cut from the same or similar material.

Figure 10:
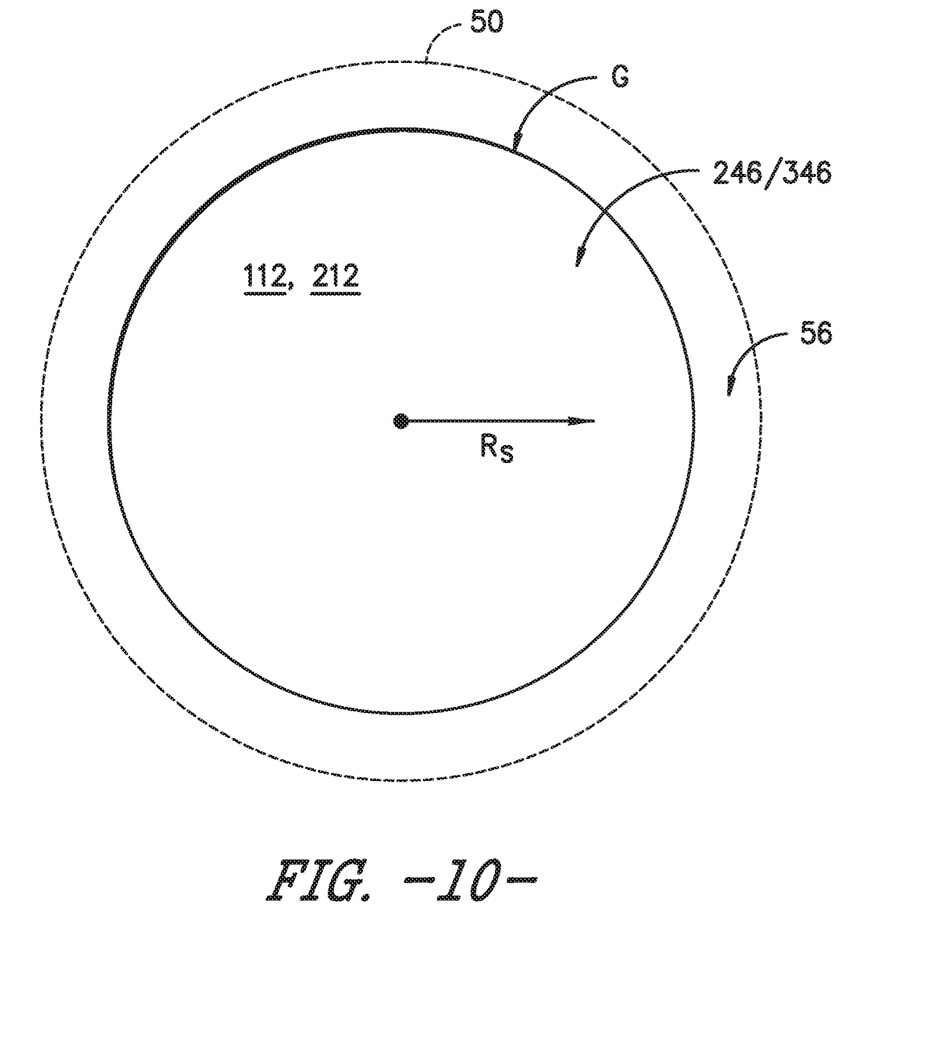
FIG. 10 is a top view of a probe facing surface of exemplary coupons of the present invention.

Also, as shown in e.g., FIGS. 2, 3, and 10 coupon 112 is carefully manufactured to minimize to size of annular gap G between the fluid contacting surface 146 and the interior surface 56 surrounding opening 62 in pipe 50. Gap G is the distance between the edge of coupon 112 and pipe 50 at fluid contacting surface 146 as measured along a line normal to the edge of coupon 112. Minimizing gap G further improves the accuracy of measurements using device 110 by minimizing fluid transport dynamics and effects cause by the interaction of fluid flow F with gap G. For example, a large gap G could cause a higher rate of corrosion of surface 146 than would otherwise be experienced by interior surface 56. In one exemplary aspect, the magnitude of gap G is in the range of 0.0025 inches to 0.0050 inches.

Coupon 112 extends longitudinally along direction LC (FIG. 3). In one exemplary aspect, coupon is symmetrical about an axis A-A extending parallel to longitudinal direction LC.

Installation, securement, and removal of coupon 112 into pocket 150 of base 116 and opening 60 of pipe 50 is facilitated with fastener 114. In this exemplary embodiment, fastener 114 includes base 116 permanently attached to pipe 50 by e.g., weld 148. Other methods may be used as well instead of weld 148. For example, attachment could be accomplished by a clamp, band strap, drill/tap, epoxy, or combinations thereof.

Base 116 includes threads 118 configured for complementary receipt of nut 120 with threads 122 (FIG. 3) whereby nut 120 is removably attached to base 116. A washer 126 includes an opening 128 though which a stem 130 of coupon 112 is inserted. Stem 130 also extends through an opening 124 in nut 120. As nut 120 is fastened to base 116, the resulting torque presses washer 126 against outer coupon shoulder 141. In turn, this presses inner coupon shoulder 140 against a seal or O-ring 144 (FIG. 3) to create a fluid tight seal against a shoulder 64 surrounding opening 60 in pipe 50. Additional O-rings 138, 142 received in grooves 134, 136 on the wider body portion 132 of coupon 112 provide additional seals. In one exemplary embodiment, the materials for construction of fastener 114 (including base 116, nut 120, and washer 126) are selected to prevent or minimize potential galvanic effects.

Notably, all components of fastener 114 are positioned outside of the equipment for this embodiment. More particularly, no portion of fastener 114 is located within pipe 50 or protrudes therein because such might interrupt the normal flow of fluid through pipe 50.

Accordingly, coupon 112 can be readily installed and removed from pipe 50. As such, after a selected period of exposure to e.g., liquid in pipe 50, coupon 112 can be removed, weighed, and otherwise inspected particularly at surface 146. A comparison of the measured weight of coupon 112 between such time intervals allows for a determination of the material deterioration to coupon 112 and, therefore, pipe 50. Additionally, fluid contacting surface 146 can be visually inspected or tested for the presence of erosion, corrosion, oxides, scaling, or other deteriorations. Because device 110 can be readily removed and replaced, the interruption of operations with pipe 50 and the exposure of fluid contacting surface 146 to air can be minimized. In addition, the relatively small size of coupon 112 allows for more precise measurements because minute changes in the weight of coupon 112 can be more readily measured.

Figure 4:
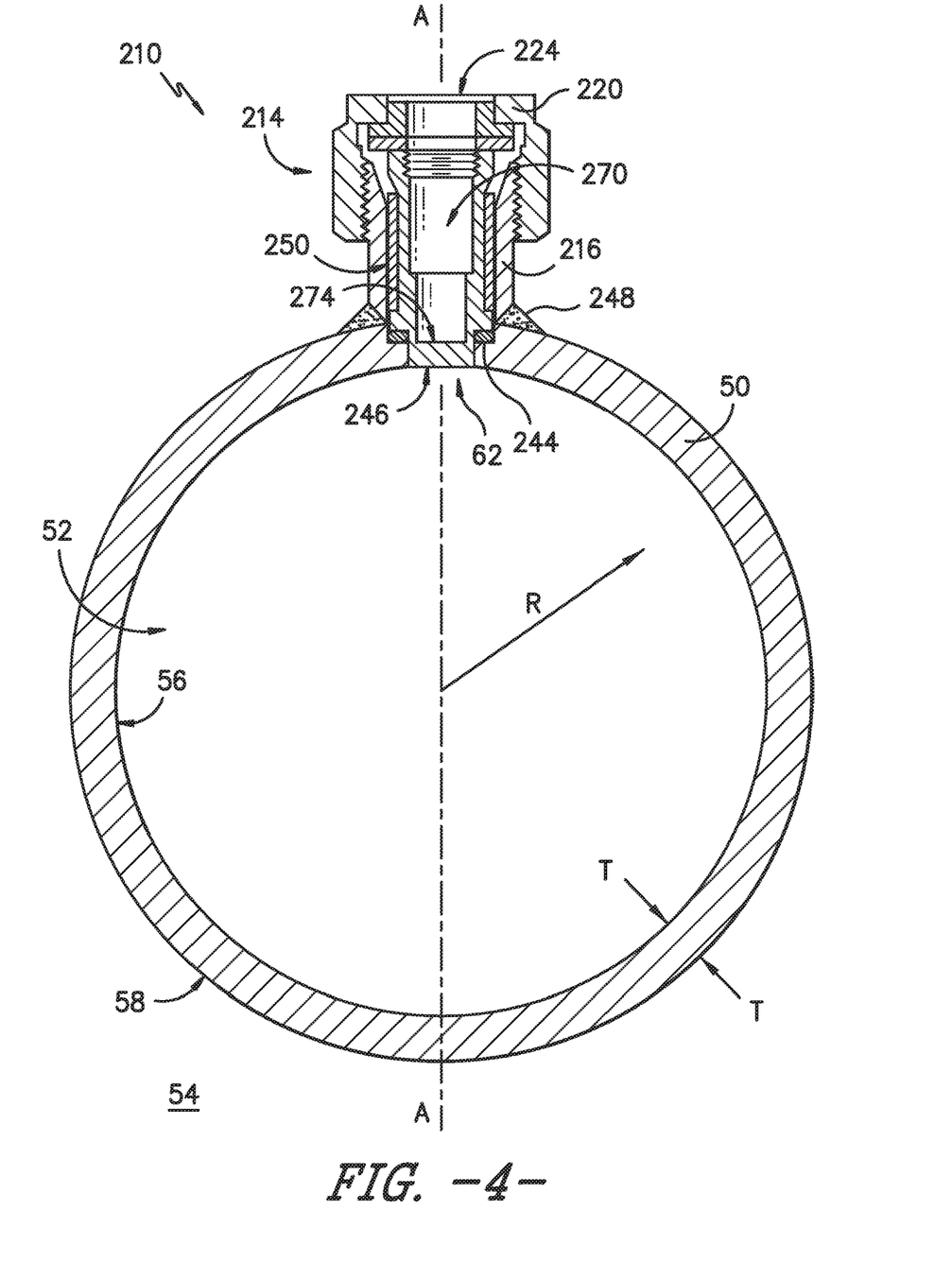
FIG. 4 is a cross-sectional view of another exemplary of the present invention installed in an example of equipment.
Figure 5:
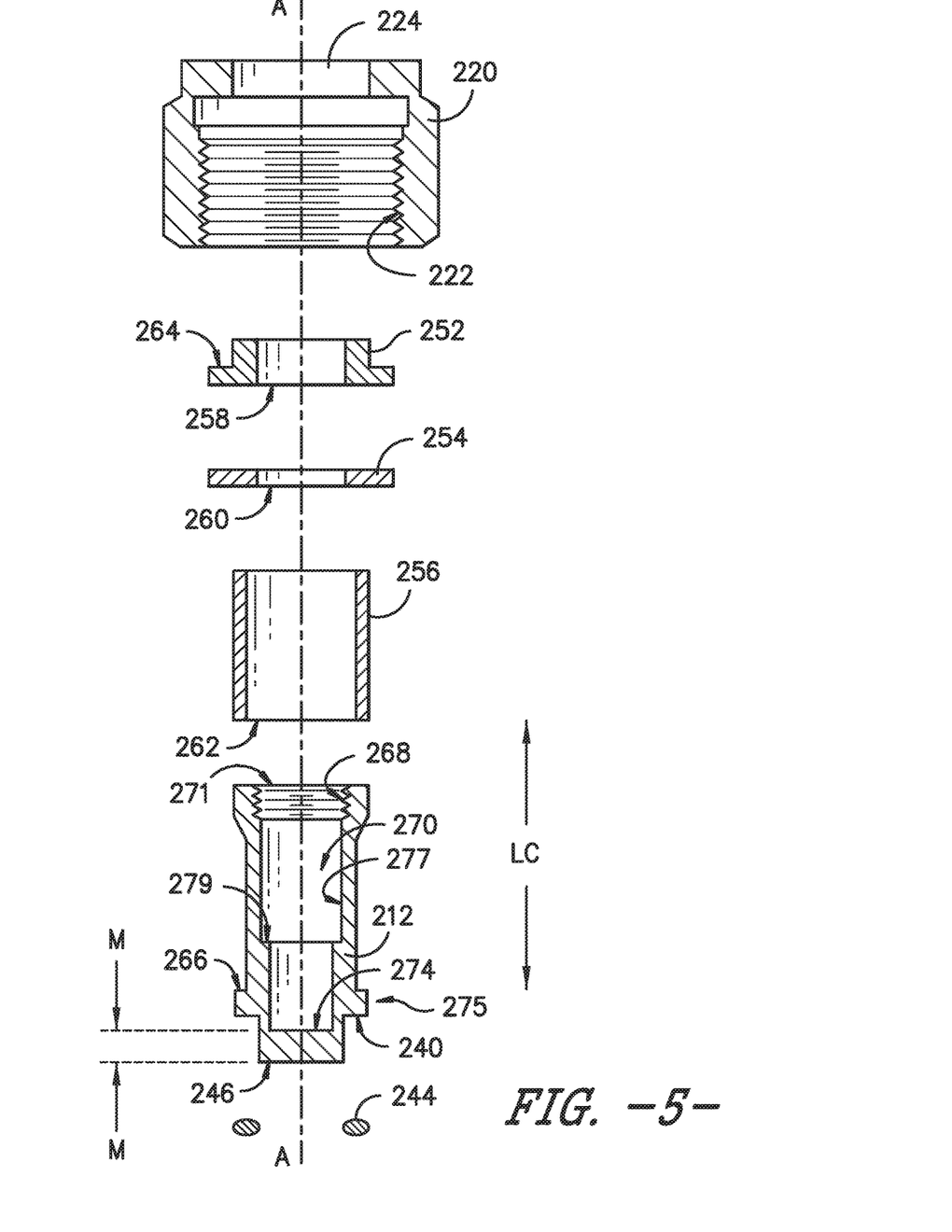
FIG. 5 is a cross-sectional and exploded view of one the exemplary embodiment of FIG. 4.
Figure 6:
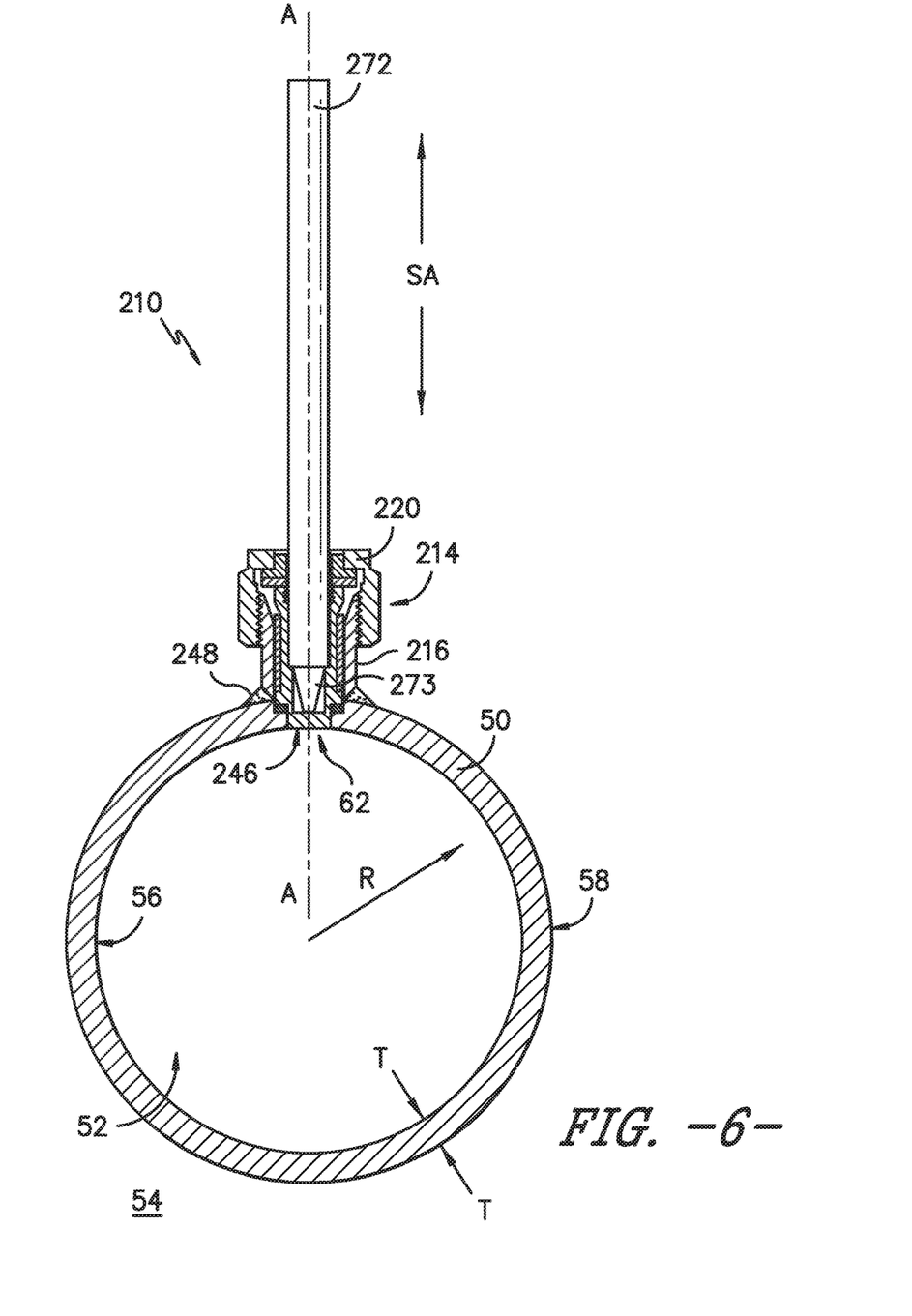
FIG. 6 is another cross-sectional view of the exemplary embodiment as in FIG. 4 and includes an exemplary probe.

FIGS. 4, 5, and 6 illustrate another exemplary embodiment of a device 210 for measuring material deterioration in equipment such as e.g., pipe 50. Device 210 is similar in construction and operation to device 110 with certain differences as will be further described. For this embodiment, device 210 includes a coupon 212 having a fluid contacting surface 246 received in opening 60 for testing and measurements as with coupon 112.

Unlike device 110, exemplary device 210 includes an internal chamber 270, which may be accessed through chamber opening 271 (FIG. 5). Chamber 270 is defined by multiple interior surfaces of coupon 212. A probe facing surface 274 is located near the tip 275 of coupon 212. Probe facing surface 274 is opposite along chamber axis AA to fluid contacting surface 246. In certain embodiments, probe facing surface 274 may also be parallel to fluid contacting surface 246 but other constructions may also be used. Coupon 212 has a predetermined thickness M (FIG. 5) between surfaces 274 and 246. In one exemplary embodiment, thickness M is e.g., $1 \text{ mm} \leq M \leq 3 \text{ mm}$. A cylindrically-shaped internal chamber surface 277 extends along the longitudinal direction LC of coupon 212 from tip 275 to opening 271 of chamber 270. For this exemplary embodiment, chamber 270 and surface 276 are symmetrical about a chamber axis A-A. As shown, chamber axis A-A is parallel to longitudinal direction LC and normal to both fluid contacting surface 246 and probe facing surface 274 for this embodiment.

FIG. 6 illustrates a probe 272, in this case an ultrasonic transducer, which is inserted through opening 224 of nut 220, opening 258 of washer 252, opening 260 of insulator 254, and into chamber 270. Probe 272 includes a shoulder that is received against internal chamber shoulder 279 (FIG. 5) of coupon 212. Probe 272 has a signal axis SA that is parallel to, and preferably coextensive with, chamber axis A-A. Fastener 214 can be used to selectively install and remove coupon 212 through opening 62 of piping 50. Fastener 214 also can be used to selectively install and remove probe 272 through chamber 270 of coupon 212.

Probe 272 is used to measure changes in the thickness M of coupon 112 caused by material deterioration. The accuracy of measuring is greatly improved by positioning probe 272 repeatably at the same position and orientation within chamber 270 during measurements. Probe 272 emits signals that travel and return along the direction of signal axis SA, which can be used to determine changes in thickness M. Inconsistencies between measurements in the angle of signal axis SA relative to chamber axis A-A or in the distance between tip 275 and surface 246 that are not due to material deterioration can reduce the accuracy of probe 272. For example, preferably when probe 272 is inserted into chamber 270, signal axis SA is always parallel (or within a range from 0 to 2 degrees) of chamber axis A-A or is at least positioned at the same angle relative to chamber axis A-A each time probe 272 is used. In one embodiment, for example, the angle is restricted to 0.255 degrees from chamber axis A-A. Similarly, preferably tip 273 of probe 272 is positioned either at the same distance from probe facing surface 274 each time probe 272 is used or in contact with surface 274 each time. In this way, accuracy can be improved because differences in the transmitted and reflected signals from probe 272 will be due to differences in thickness M rather than variations in the location and orientation of probe 272 relative to e.g., fluid contacting surface 146. Additionally, where surface 246 and 274 are parallel, the precision of measurements with probe 272 may be improved because the signal is more efficiently reflected back to probe 272.

Accordingly, the construction of chamber 270 and fastener 214 helps secure the alignment of the signal axis SA with chamber axis A-A. Such construction ensures that e.g., ultrasonic signals emitted from the tip 273 of probe 272 are repeatably directed along a path normal to both fluid contacting surface 246 and probe facing surface 274. Furthermore, chamber 270 and fastener 214 ensure that probe 272 can be repeatedly positioned at the same place and orientation (or close thereto) relative to both fluid contacting surface 246 and probe facing surface 274 each time probe 272 is installed into chamber 270. Thickness M of tip 275 is maintained relatively thin so that small changes can be readily measured by probe 272 and/or by measuring changes in the weight of coupon 212.

Additionally, the inner surface 277 of chamber 270 around tip 273 of probe 272 has a linear profile below shoulder 279 along longitudinal direction LC (FIG. 5) to minimize potential reflective surfaces that could introduce error when using probe 272. In another exemplary aspect, thickness M of tip 275 is less than thickness T of pipe 50. This allows tip 273 of probe 272 to be positioned into opening 60 below exterior surface 58 so as to further reduce the possibility of improperly reflecting a signal from equipment 50 to probe 272.

As with device 110, coupon 212 of device 210 can be readily and quickly removed and installed using fastener 214 such that coupon 212 can be weighed and fluid contacting surface 246 can be inspected or tested for material deterioration. During such installation and removal, protection of coupon 212 from incidental damage is desirable. For example, scratching or denting coupon 212 against fastener 214 or pipe 50 could change the weight of coupon 212 and thereby adversely affect the accuracy of weight measurements used to determine whether material deterioration has occurred. In this exemplary embodiment, coupon 212 is provided with a sleeve 256 having an opening 262 for receipt of coupon 212 therein. Sleeve 212 can be constructed from e.g., polytetrafluoroethylene, an acetal resin, a plastic, or some other material that will protect coupon 212 during installation and removal from opening 60 in pipe 50 and pocket 250 in base 216.

Figure 7:
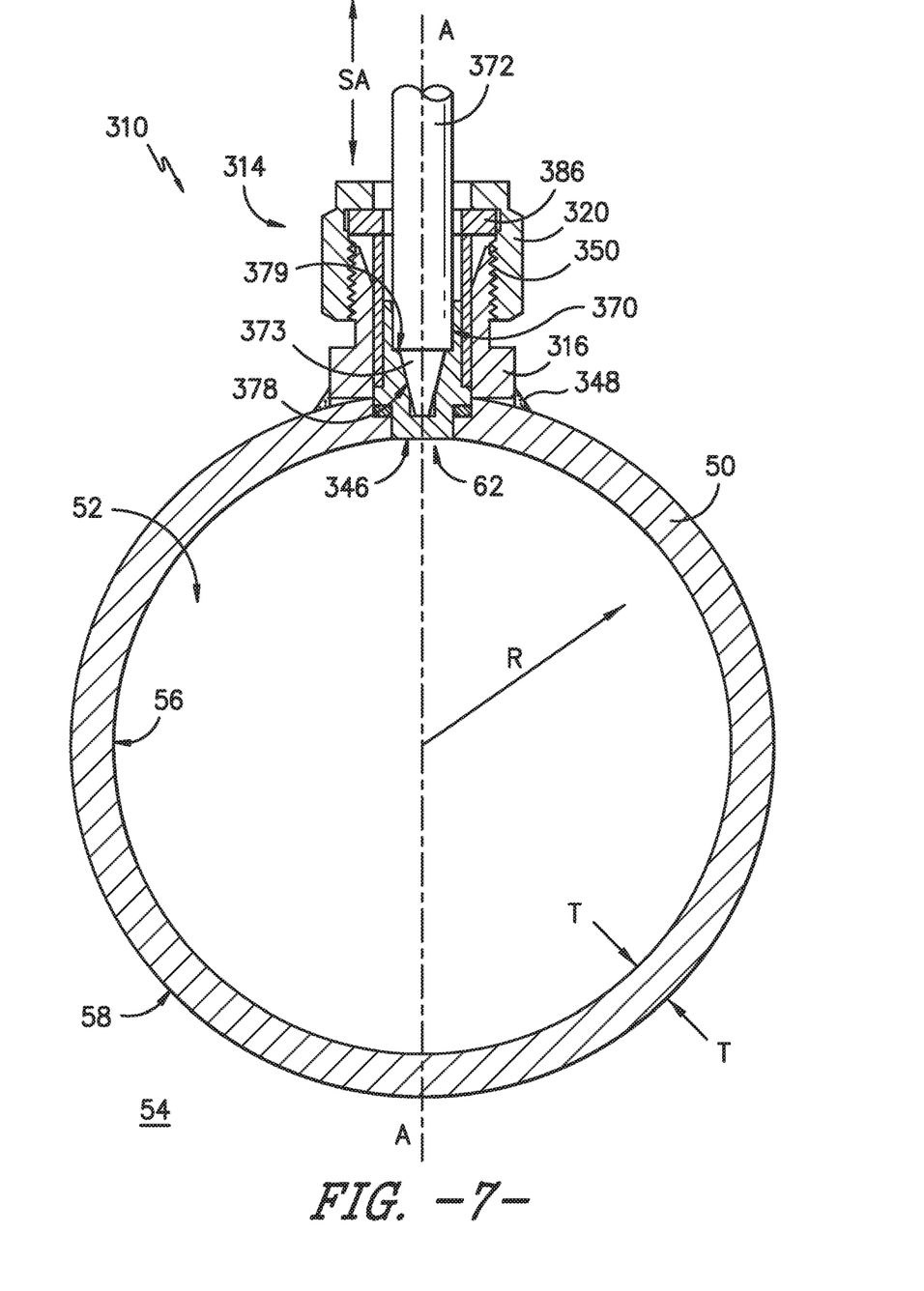
FIG. 7 is a cross-sectional view of another exemplary of the present invention installed in an example of equipment.
Figure 8:
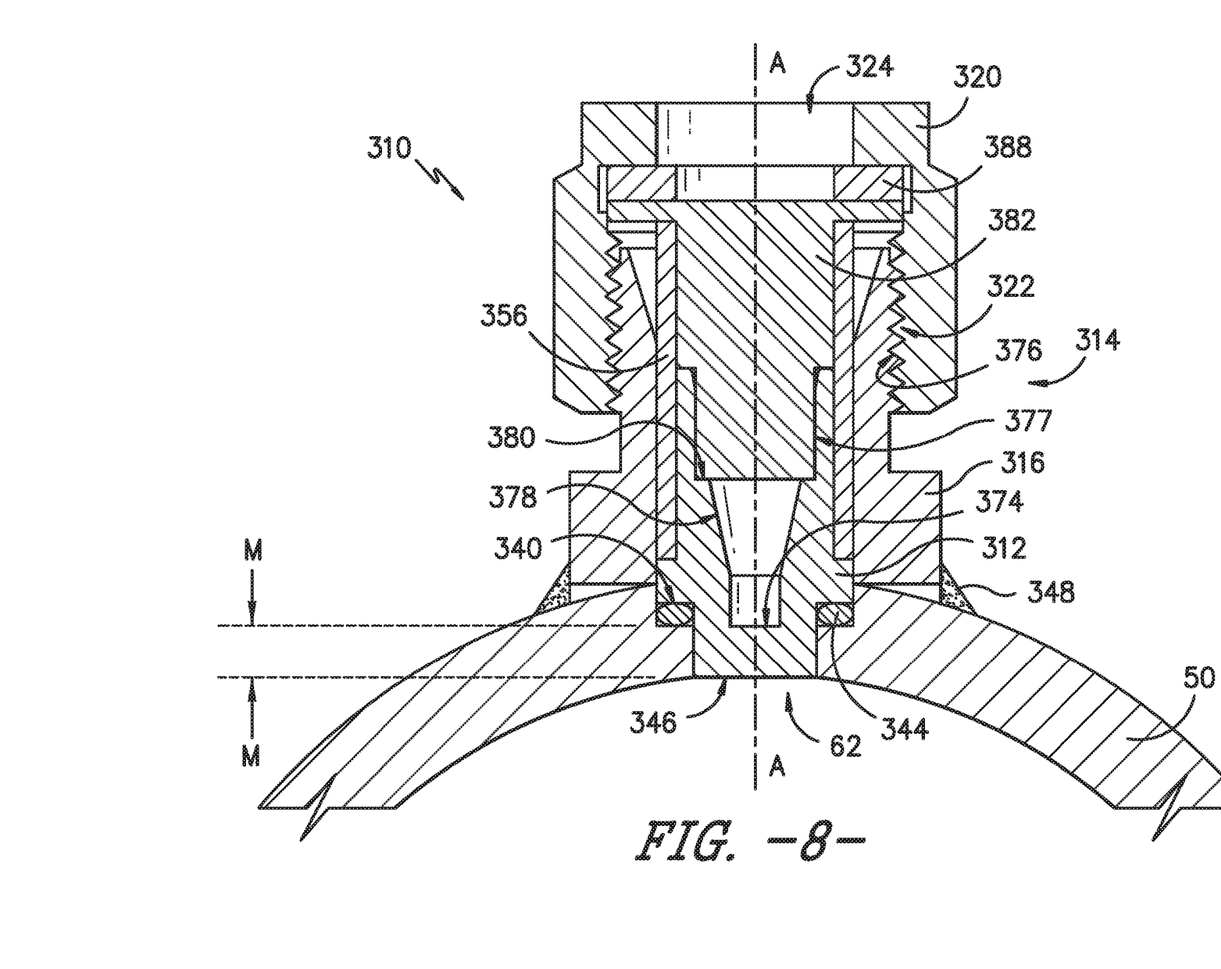
FIG. 8 is a close-up, cross-sectional view of the exemplary embodiment of FIG. 7 with an exemplary plug installed.
Figure 9:
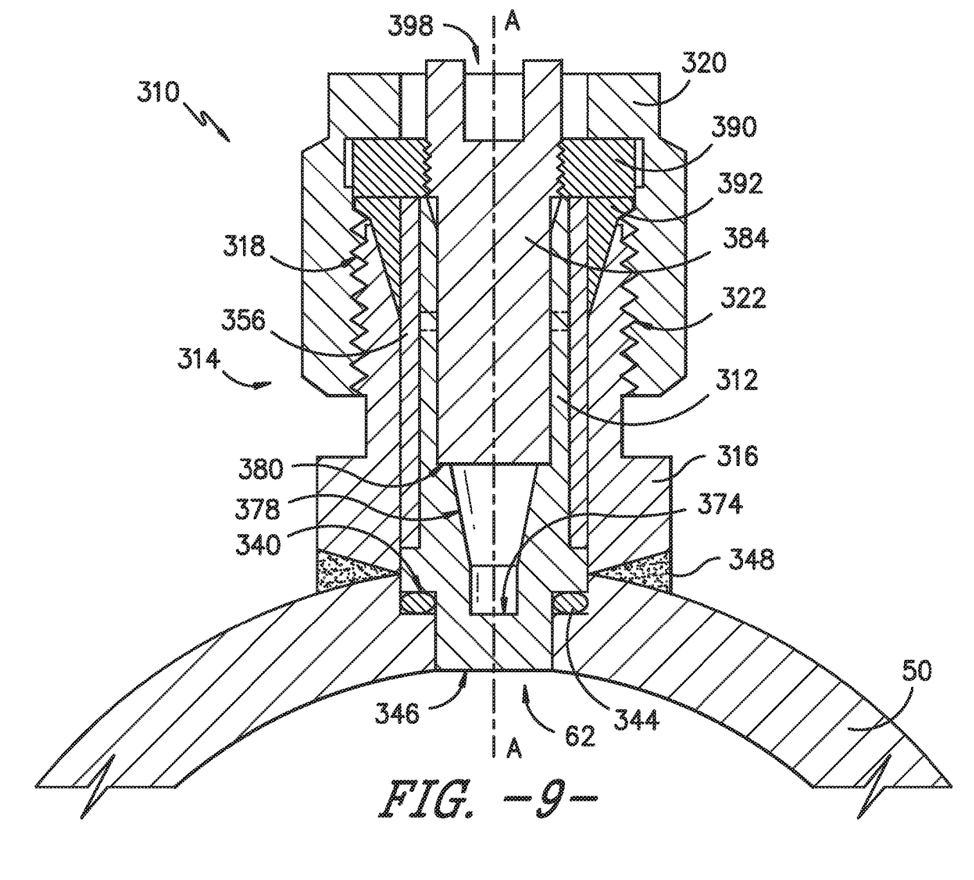
FIG. 9 is a close-up, cross-sectional view of the exemplary embodiment of FIG. 7 with another exemplary plug installed.

FIGS. 7, 8, and 9 illustrate still another exemplary embodiment of a device 310 for measuring material deterioration in equipment. Device 310 is similar in construction and operation to devices 110 and 210 with certain differences as will be further described. Device 310 is similar to device 210 in that it can be used with a probe 372 such as e.g., an ultrasonic transducer removably inserted into chamber 370 of coupon 312 and secured with fastener 314. The internal surface of chamber 370 includes a cylindrically-shaped surface 377 adjacent (along chamber axis A-A) to frustoconically-shaped surface 378, which is configured for complementary receipt of tip 373 of probe 372. Surface 378 assists in aligning the signal axis SA of probe 372 with chamber axis A-A so that signals emitted to and from 373 travel along a path normal to fluid contacting surface 346 and probe facing surface 374 as previously described. Surface 378 may not actually contact tip 373 once probe 372 is secured in place. The symmetrical shape of surface 378 about chamber axis A-A also helps minimize potential reflective surfaces that could introduce error when using probe 272. Coupon 312 otherwise has features similar to coupons 112 and 212.

When probe 372 is not in place within chamber 370, a plug can be used to protect coupon 312 from damage that could affect e.g., weight measurements. Accordingly, FIG. 8 illustrates a plug 382 that can be used with washer 388 to protect coupon 312. FIG. 9 illustrates another embodiment of a plug 384 with washers 390 and 392 that may be used to protect coupon 312.

FIG. 10 provides a view of probe facing surfaces 274, 374 for exemplary coupons 212, 312. To increase the precision and accuracy of signals reflected back to probe 272, 372, in one exemplary aspect, probe facing surfaces 274, 374 have a certain "flatness" that helps improve the consistency in reflected signals. As used herein, "flatness" is defined as the distance between two hypothetical parallel planes within which any one of probe facing surfaces 274 and 374 could be entirely located. Thus, for a given probe facing surface 274 or 374, such surface becomes flatter as the specified distance between these two planes decreases.

Accordingly, referring to FIG. 10, within at least a 2 mm radius $R_C$ of chamber axis A-A, in certain exemplary embodiments of coupon 212 or 312, probe facing surface 274 or 374 has a flatness within a tolerance of 0.5 mm or less. In still other embodiments, probe facing surface 274 or 374 has a flatness within a tolerance of 0.1 mm or less. In yet still other embodiments, probe facing surface 274 or 374 has a flatness within a tolerance of 0.00008 inch or less (0.0002 mm or less).

In the figures, coupons 112, 212, and 312 are shown as cylindrical in shape, which may be more readily manufactured. However, using the teachings disclosed herein, it will be understood that non-cylindrical coupons may also be used. In such case, a circular or cylindrical chamber can be provided as described for insertion of a probe.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A device for measuring material deterioration in equipment, comprising:
    a coupon configured for selective insertion and removal through an opening in the equipment, the coupon comprising
        a tip providing a fluid contacting surface for positioning within an interior of an equipment and in contact with fluid; and
        a chamber internal to the coupon and having an opening for access thereto, the chamber defined at least in part by a probe facing surface positioned opposite to the fluid contacting surface and facing the opening, the chamber separated by the tip from fluid in the equipment at the fluid contacting surface; and
    a fastener configured for selectively affixing the coupon to the equipment, the fastener positioned outside of the equipment.

2. The device for measuring material deterioration in equipment as in claim 1, wherein the fluid contacting surface is positioned flush with an interior surface of the equipment adjacent to the fluid contacting surface.

3. The device for measuring material deterioration in equipment as in claim 1, wherein the chamber is symmetrical about a chamber axis extending normal to the probe facing surface.

4. The device for measuring material deterioration in equipment as in claim 3, wherein within a 2 mm radius of the chamber axis the probe facing surface has a flatness within a tolerance of 0.0002 mm or less.

5. The device for measuring material deterioration in equipment as in claim 1, wherein the fluid contacting surface is contoured to match a shape of an interior surface of the equipment surrounding the fluid contacting surface.

6. The device for measuring material deterioration in equipment as in claim 1, wherein the internal chamber is defined by one or more internal surfaces configured for orienting a transducer positioned within the chamber such that the transducer will emit signals along a direction normal to the probe facing surface.

7. The device for measuring material deterioration in equipment as in claim 1, further comprising
    an ultrasonic transducer positioned within the chamber and oriented so that signals are emitted from the ultrasonic transducer along a direction normal to the probe facing surface.

8. The device for measuring material deterioration in equipment as in claim 7, wherein the internal chamber is further defined by a frustoconical surface configured for complementary receipt of the ultrasonic transducer.

9. The device for measuring material deterioration in equipment as in claim 1, wherein the fastener comprises a sleeve surrounding at least a portion of the coupon.

10. The device for measuring material deterioration in equipment as in claim 1, wherein the fastener comprises:
    a base attached to the equipment; and
    a nut removably attached to the base.

11. The device for measuring material deterioration in equipment as in claim 10, wherein the fastener comprises a sleeve surrounding at least a portion of the coupon and pressed between the base and the nut when the nut is attached to the base.

12. The device for measuring material deterioration in equipment as in claim 11, wherein the sleeve comprises polytetrafluoroethylene.

13. The device for measuring material deterioration in equipment as in claim 11, wherein the sleeve comprises an acetal resin.

14. The device for measuring material deterioration in equipment as in claim 1, wherein the equipment has a wall thickness at the opening where the coupon is inserted, and wherein a thickness of the coupon between the probe facing surface and the fluid contacting surface is less than the wall thickness.

15. A device for measuring material deterioration in equipment, comprising:
    a coupon configured for insertion and removal through an opening in an equipment, the opening having a surrounding interior surface defined by the equipment and formed from an equipment material, the coupon comprising
        a fluid contacting surface for positioning within an interior of the equipment and in contact with a fluid, wherein the fluid contacting surface is flush with the surrounding interior surface of the equipment, the fluid contacting surface consisting of material having a same composition as the equipment material; and
        a fastener configured for selectively affixing the coupon to the equipment, the fastener positioned outside of the equipment;
    wherein a gap is formed between the fluid contacting surface and the surrounding interior surface, the gap being in the range of 0.0025 inches to 0.0050 inches.

16. The device for measuring material deterioration in equipment as in claim 15, wherein the coupon has a longitudinal axis about which the coupon is symmetrical.

17. The device for measuring material deterioration in equipment as in claim 15, wherein the fluid contacting surface is contoured to match a shape of an interior surface of the equipment surrounding the fluid contacting surface.

18. The device for measuring material deterioration in equipment as in claim 15, wherein the coupon defines a tip and a chamber separated from the fluid by the tip.

19. A device for measuring material deterioration in equipment, comprising:
    a coupon configured for insertion and removal through an opening in the equipment, the opening of the equipment having a surrounding interior surface formed from a material of the equipment that has an equipment material composition, the coupon comprising:
        a tip defining a fluid contacting surface for positioning within an interior of an equipment in contact with a fluid in the equipment, the fluid contacting surface flush with the surrounding interior surface of the equipment, the fluid contacting surface consisting of a material having a composition that is the same as the equipment material composition, the tip also defining a probe facing surface positioned opposite to the fluid contacting surface along a longitudinal axis of the coupon; and
        a fastener configured for selectively affixing the coupon to the equipment, the fastener positioned outside of the equipment.

20. The device of claim 19, wherein the coupon defines a chamber separated from the fluid in the equipment by the tip.

* * * * *